United States Patent [19]

Sasse et al.

[11] 3,989,710
[45] Nov. 2, 1976

[54] CERTAIN 2-MERCAPTO-4,5-DICHLORO-THIAZOLE COMPOUNDS

[75] Inventors: Klaus Sasse, Schildgen; Gunther Beck, Leverkusen; Ludwig Eue, Cologne, all of Germany

[73] Assignee: Bayer Aktiengesellschaft, Leverkusen, Germany

[22] Filed: Aug. 14, 1974

[21] Appl. No.: 497,356

[30] Foreign Application Priority Data

Sept. 1, 1973 Germany............................ 2344134

[52] U.S. Cl................................ 260/302 H; 71/90; 260/302 S
[51] Int. Cl.[2]........................................ C07D 277/36
[58] Field of Search..................... 260/302 S, 302 H

[56] References Cited
UNITED STATES PATENTS

| | | | |
|---|---|---|---|
| 2,697,098 | 12/1954 | Levis ............................... | 260/302 S |
| 2,721,868 | 10/1955 | D'Amico ......................... | 260/302 S |
| 2,766,253 | 10/1956 | Downey et al................... | 260/302 S |
| 3,481,946 | 12/1969 | Schmidt et al.................. | 260/302 S |

*Primary Examiner*—R. Gallagher
*Attorney, Agent, or Firm*—Burgess, Dinklage & Sprung

[57] ABSTRACT

Novel carbonic acid derivatives of 2-mercapto-4,5-dichloro-thiazole which has the formula

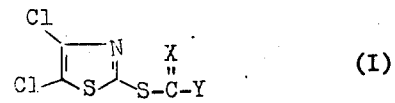

(I)

in which
X is oxygen or sulfur
Y is a radical -OR, -SR or

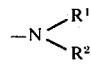

are outstandingly effective herbicides exhibiting particularly pronounced post-emergence activity.

17 Claims, No Drawings

CERTAIN 2-MERCAPTO-4,5-DICHLORO-THIAZOLE COMPOUNDS

The present invention relates to certain new carbonic acid compounds of 2-mercapto-4,5-dichloro-thiazole, to herbicidal compositions containing them and to their use as herbicides.

It is known that carbonic acid esters of 2-mercapto-benzimidazole of 2-mercapto-benzothiazole and of 2-mercapto-benzoxazole exhibit fungicidal properties, from German Patent Specification 961,169. Furthermore, it has been disclosed that carbonic acid esters of 2,3-dimercapto-quinoxaline exhibit fungicidal and acaricidal activity, from German Patent Specification 1,088,965. However, a use of the above-mentioned compounds as herbicides has not been described hitherto.

Furthermore, it is already known that thiocarbamic acid esters in which the sulfur atom is bonded to an alkyl group or aralkyl group exhibit herbicidal properties. The activity of these compounds is however not always entirely satisfactory, especially if they are used by the post-emergence process.

The present invention provides, as new compounds, the carbonic acid derivatives of 2-mercapto-4,5-dichloro-thiazole of the general formula

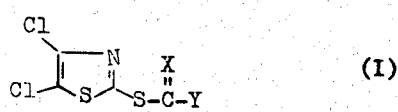   (I)

in which
X is oxygen or sulfur,
Y is radical -OR, -SR or

R is alkyl of from 1 to 12 carbon atoms, alkenyl of from 2 to 12 carbon atoms or alkynyl of from 3 to 12 carbon atoms (each of the aforesaid radicals optionally being substituted by one or more substituents selected from halogen, alkoxy, aryloxy, alkylmercapto and arylmercapto), aralkyl of from 1 or 2 aryl radicals on the alkyl moiety and 1 to 4 carbon atoms in the alkyl moiety (the aryl moiety optionally being substituted by one or more substituents selected from halogen, alkyl, haloalkyl, nitro, alkoxy, alkylmercapto and nitrile), cycloalkyl of from 4 to 8 carbon atoms (the ring optionally being substituted by alkyl and/or containing a fused ring), or aryl (optionally being substituted by one or more substituents selected from halogen, alkyl, haloalkyl, nitro, alkoxy, alkylmercapto, dialkylamino, carbalkoxy, N,N-dialkylcarbamoyl and nitrile), and R¹ and R², which may be identical or different, are each hydrogen, alkyl of from 1 to 12 carbon atoms (optionally being substituted by one or more substituents selected from alkoxy, hydroxyl, alkylmercapto, aryloxy, arylmercapto, nitrile, carbalkoxy and N,N-dialkylcarbamoyl), alkenyl of from 2 to 5 carbon atoms, alkynyl of from 3 to 12 carbon atoms, cycloalkyl of from 3 to 8 carbon atoms, aralkyl of from 1 or 2 aryl radicals on the alkyl moiety and 1 to 4 carbon atoms in the alkyl moiety (the aryl moiety optionally being substituted by one or more substituents selected from alkyl, alkoxy, alkylmercapto, halogen, haloalkyl, nitro and dialkylamino), or aryl (optionally being substituted by one or more substituents selected from halogen, alkyl, haloalkyl, alkoxy, alkylmercapto and nitro),
or
R¹ and R² conjointly with the adjoining nitrogen atom form a three-membered to seven-membered ring in which one or two carbon atoms can be replaced by oxygen, sulfur or nitrogen, or
X and Y conjointly represent a triply bonded nitrogen atom.

The compounds of formula (I) have been found to exhibit very good herbicidal properties.

In contrast to the known carbonic acid derivatives of heterocyclic compounds containing mercapto groups, which are predominantly fungicidally active, the carbonic acid derivatives of 2-mercapto-4,5-dichloro-thiazole, according to the present invention, are, surprisingly, highly active herbicides. In contrast to the known thiocarbamic acid esters with alkyl and aralkyl groups on the sulfur atom, which have particularly a pre-emergence effect and essentially act against grass-like weeds, the compounds according to the present invntion particularly display their action in post-emergence use, frequently without any residual action through the soil. Given this pattern of action, the compounds according to the invention represent a valuable enrichment of the art.

The present invention also provides a process for the preparation of a carbonic acid derivative of 2-mercapto-4,5-dichloro-thiazole of the general formula (I), in which
a. 2-mercapto-4,5-dichloro-thiazole of the formula:

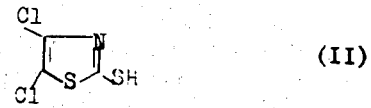   (II)

is reacted, in the presence of the acid-binding agent or in the form of a metal salt thereof, with a halogen compound of the general formula:

   (III), in which
X and Y have the above-mentioned meanings and
Hal is chlorine or bromine, in the presence of a diluent, or
b. a 4,5-dichloro-thiazole compounds of the general formula:

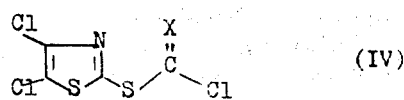   (IV)

in which

X has the above-mentioned meaning, is reacted with an alcohol, phenol, mercaptan, thiophenol or amine of the general formula:

H - Y        (V), in which

Y has the above-mentioned meaning, in the presence of an acid-binding agent and in the presence of a diluent.

If 2-mercapto-4,5-dichloro-thiazole and carbonic acid methyl ester chloride are used as starting compounds, the course of the reaction according to process variant (a) can be represented by the following equation:

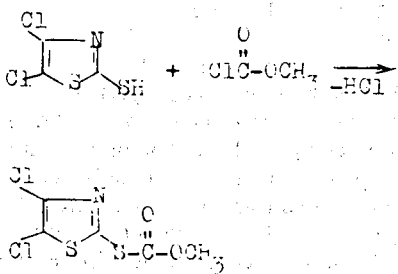

If 2-chlorocarbonylmercapto-4,5-dichloro-thiazole and dimethylamine are used as starting compounds, the course of the reaction according to process variant (b) can be represented by the following equation:

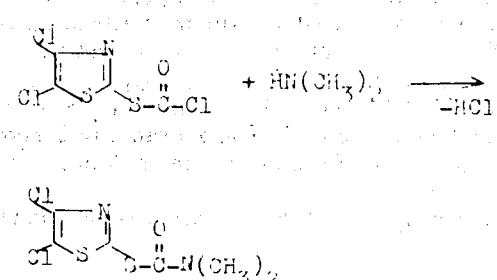

2-Mercapto-4,5-dichloro-thiazole, designated by the formula (II), has not previously been described in the literature. It may be obtained by reaction of 2,4,5-trichlorothiazole with a salt of hydrogen sulfide, especially an alkali metal hydrogen sulfide, in accordance with the following equation:

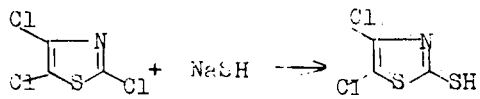

The reaction is preferably carried out in aqueous solution, it being possible to add a water-miscible solvent, such as acetone, dioxane, tetrahydrofuran and the like, as a solubilizing agent. The reaction temperature is generally between 0° C and 130° C and preferably between 10° and 90° C.

2,4,5-Trichloro-thiazole is obtainable (in accordance with German Published Patent Application 2,213,865) by sulfurization of pentachloroethyl- or trichlorovinyl-isocyanodichloride. This reaction is carried out in the temperature range of 150° to 350° C using approximately the stoichiometrically required amount of sulfur, and preferably without a solvent.

The starting compounds of general formula (III) are known in principle. If particular compounds have not yet been described, they can be prepared according to known processes. As examples there may be mentioned: carbonic acid methyl ester chloride, carbonic acid ethyl ester chloride, carbonic acid propyl ester chloride, carbonic acid isopropyl ester chloride, carbonic acid butyl ester chloride, carbonic acid isobutyl ester chloride, carbonic acid sec.-butyl ester chloride, carbonic acid tert.-butyl ester chloride, carbonic acid pentyl ester chloride, carbonic acid octyl ester chloride, carbonic acid ester dodecyl ester chloride, carbonic acid 2-chloro-ethyl ester chloride, carbonic acid 2,2,2-trichloroethyl ester chloride, carbonic acid 1,2,2,2-tetrachloroethyl ester chloride, carbonic acid 1,3-dichloro-isopropyl ester chloride, carbonic acid 2,2,2-tribromoethyl ester chloride, carbonic acid 2,3-dibromo-propyl ester chloride, carbonic acid 2-methoxy-ethyl ester chloride, carbonic acid 2-isopropoxy-ethyl ester chloride, carbonic acid 2-phenoxyethyl ester chloride, carbonic acid 4-methoxy-butyl ester chloride, carbonic acid 2-methylmercapto-ethyl ester chloride, carbonic acid 2-phenylmercapto-ethyl ester chloride, carbonic acid 2-(4-chloro-phenylmercapto)-ethyl ester chloride, carbonic acid allyl ester chloride, carbonic acid crotyl ester chloride, carbonic acid 2-methyl-buten-(3)-yl-(2) ester chloride, carbonic acid propargyl ester chloride, carbonic acid butyn-(1)-yl-(3) ester chloride, carbonic acid 2-methyl-butyn-(3)-yl-(2) ester chloride, carbonic acid 1,4-butylene bis-ester chloride, carbonic acid benzyl ester chloride, carbonic acid 4-chloro-benzyl ester chloride, carbonic acid 2,6-dichloro-benzyl ester chloride, carbonic acid 4-methyl-benzyl ester chloride, carbonic acid 4-trifluoromethyl-benzyl ester chloride, carbonic acid 4-nitrobenzyl ester chloride, carbonic acid 4-methoxy-benzyl ester chloride, carbonic acid 4-methylmercapto-benzyl ester chloride, carbonic acid 4-cyanobenzyl ester chloride, carbonic acid 2-phenyl-ethyl ester chloride, carbonic acid 3-phenyl-propyl ester chloride, carbonic acid diphenylmethyl ester chloride, carbonic acid 1,2-diphenyl-ethyl ester chloride, carbonic acid cyclobutyl ester chloride, carbonic acid cyclopentyl ester chloride, carbonic acid cyclohexyl ester chloride, carbonic acid cyclohexylmethyl ester chloride, carbonic acid tetralyl- (1) ester chloride, carbonic acid phenyl ester chloride, carbonic acid 2-chlorophenyl ester chloride, carbonic acid 4-chlorophenyl ester chloride, carbonic acid 2,4-dichloro-phenyl ester chloride, carbonic acid pentachlorophenyl ester chloride, carbonic acid 4-methylphenyl ester chloride, carbonic acid 2-methyl-4-chloro-phenyl ester chloride, carbonic acid 4-isopropyl-phenyl ester chloride, carbonic acid 2,6-di-tert.-butyl-phenyl ester chloride, carbonic acid 3-trifluoromethyl-phenyl ester chloride, carbonic acid 4-nitro-phenyl ester chloride, carbonic acid 4-methoxy-phenyl ester chloride, carbonic acid 3-methyl-4-methylmercapto-phenyl ester chloride, carbonic acid 4-dimethylamino-phenyl ester chloride hydrochloride, carbonic acid 4-carbethoxy-phenyl ester chloride, carbonic acid 4-N,N-dimethylcarbamoyl-phenyl ester chloride, carbonic acid 4-cyano-phenyl ester chloride, carbonic acid naphthyl-(1)ester chloride, carbonic acid naphthyl-(2) ester chloride, thiocarbonic acid S-methyl ester chloride, thiocarbonic acid S-ethyl ester chloride, thiocarbonic acid S-propyl ester chloride, thiocarbonic acid S-isopropyl ester chloride, thiocarbonic acid S-butyl ester chloride, thiocarbonic acid S-dodecyl ester chloride, thiocarbonic acid S-benzyl ester chloride, thiocarbonic acid S-4-chloro-benzyl-ester chloride, thiocarbonic acid S-3,4-dichloro-benzyl ester chloride, thiocarbonic acid S-phenyl ester chloride, thiocarbonic acid S-4-chloro-phenyl ester chloride, thiocarbonic acid S-4-methyl-phenyl ester chloride, thiocarbonic acid O-ethyl ester chloride, thiocarbonic acid O-butyl ester chloride, thiocarbonic acid O-phenyl ester chloride, dithiocarbonic acid ethyl ester chloride, dithiocarbonic acid butyl ester chloride, dithiocarbonic acid benzyl ester chloride, dithiocarbonic acid phenyl ester chloride, N,N-dimethyl-carbamic acid chloride, N,N-diethyl-carbamic acid chloride, dipropyl-carbamic acid chloride, di-isopropyl-carbamic acid chloride, dibutyl-carbamic acid chloride, N-methyl-N-isopropyl-carbamic acid chloride, M-methyl-N-dodecyl-carbamic acid chloride, N-methyl-N-2-methoxy-ethyl-carbamic acid chloride, N-methyl-N-2-methylmercapto-ethyl-carbamic acid chloride, N-methyl-N-2-phenoxyethyl-carbamic acid chloride, bis-2-cyano-ethyl-carbamic acid chloride, diallylcarbamic acid chloride, dicyclohexylcarbamic acid chloride, N-methyl-N-cyclohexylcarbamic acid chloride, N-methyl-N-phenyl-carbamic acid chloride, N-methyl-N-4-chloro-phenyl-carbamic acid chloride, N-methyl-N-4-methyl-phenyl-carbamic acid chloride, N-methyl-N-4-methoxy-phenyl-carbamic acid chloride, N-methyl-N-4-methylmercapto-phenyl-carbamic acid chloride, N-methyl-N-4-nitro-phenyl-carbamic acid chloride, pyrrolidine-1-carboxylic acid chloride, piperidine-1-carboxylic acid chloride, hexamethyleneimine-1-carboxylic acid chloride, tetrahydroquinoline-1-carboxylic acid chloride, imidazole-1-carboxylic acid chloride, 1,2,4-triazole-2-carboxylic acid chloride, morpholine-4-carboxylic acid chlorine, thiamorpholine-4-carboxylic acid chloride, dimethyl-thiocarbamic acid chloride, diethyl-thiocarbamic acid chloride, dipropyl-thiocarbamic acid chloride, piperidine-1-thiocarboxylic acid chloride, morpholine-4-thiocarboxylic acid chloride, cyanogen chloride and cyanogen bromide.

The 2-chlorocarbonylmercapto- and 2-chlorothiocarbonylmercapto-4,5-dichloro-thiazoles of formula (IV), required as the starting material according to process variant (b), have not been described previously in the literature. They may be obtained by the action of phosgene or thiophosgene on a dry alkali metal salt of 2-mercapto-4,5-dichloro-thiazole (formula II) in accordance with the following equation:

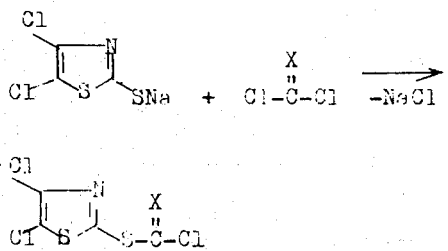

(wherein X has the above-mentioned meaning).

The preferred procedure followed here is to introduce the alkali metal salt of 2-mercapto-4,5-dichlorothiazole in portions, in not more than the stoichiometric amount, into a solution of phosgene or thiophosgene in an inert solvent such as benzene, toluene, dichloromethane, chloroform, carbon tetrachloride, ether or dioxane. The reaction temperature is preferably 0° –50° C. After filtering off the salt which was separated out, the reaction product (IV) is isolated by evaporating off the solvent.

The alcohols, phenols, mercaptans, thiophenols and amines of formula (V) required as starting materials are known in principle.

The reaction between the 2-mercapto-4,5-dichlorothiazole (II) and the carbonic acid halide (III) in accordance with process variant (a) is preferably carried out in the presence of a diluent. As diluents, it is possible to use those which do not react more rapidly with the carbonic acid halides (II) than does 2-mercapto-4,5-dichloro-thiazole, for example hydrocarbons, such as benzene and toluene, chlorinated hydrocarbons such as chloroform, carbon tetrachloride and chlorobenzene, ethers such as diethyl ether, dioxane and tetrahydrofuran, ketones such as acetone and cyclohexanone and carboxylic acid esters such as ethyl acetate. The reaction can also be carried out in water as the sole diluent or in the presence of water, for example also in mixtures of water and water-miscible solvents, such as acetone or dioxane, or in the two-phase system of water and a water-insoluble solvent.

An acid-binding agent is required to bind the hydrogen halide liberated in the reaction according to process variant (a). For this purpose, it is possible to use alkali metal hydroxides, carbonates and acetates, alkaline earth metal hydroxides, oxides and carbonates and tertiary amines such as pyridine, triethylamine, N,N-dimethylaniline, hexahydrodimethylaniline and the like. It is also possible, instead of adding an acid-binding agent to the two reactants, to react metal salts of 2-mercapto-5,6-dichloro-thiazole directly with the carbonic acid halides of the formula (III), for which purpose it is possible to use not only the alkali metal salts and alkaline earth metal salts but also other metal salts, for example those of lead, copper or silver. Such salts are obtained in the usual manner by stirring 2-mercapto-4,5-dichlorothiazole with the corresponding metal oxides, hydroxides or, alcoholates or, for example, by ionic double decomposition of the alkali metal salts or alkaline earth metal salts of 2-mercapto-4,5-dichloro-thiazole with the salt of an appropriate metal.

The reaction temperature can be varied within wide limits. In general, the reaction should be carried out at between −20° and +120° C, preferable at from 0° to 60° C. Generally, the reactions are carried out under normal pressure but it is also possible to carry them out in a closed vessel in which a correspondingly higher pressure then becomes established, depending on the nature of the solvent and on the temperature.

The reactants are preferably reacted with one another in the stoichiometrically equimolar ratio, and preferably the acid-binding agent is also present in the equimolar amount although higher amounts of the acid-binding agent do not have an adverse influence on the yield of reaction product provided that excessively elevated temperatures are not used.

The sequence in which the two reactants and the acid-binding agent are brought together is not critical to the success of the reaction provided that the reaction of the carbonic acid halide with the acid-binding agent in the absence of sufficient amounts of 2-mercapto-4,5-dichlorothiazole is avoided.

The reaction batches are worked up in the usual manner, for example by filtering off the reaction products which precipitate directly from the reaction mixture, by precipitating them by adding water or by isolating them from solutions through distilling off the solvent, after which a subsequent wash with water is as a rule necessary to remove salt-like admixtures.

The same conditions apply to the preparation of the compounds of the formula (I) in accordance with process varient (b), as for the reactions according to process varient (a), as far as the diluents, the amounts of the reactants, the acid-binding agent, the reaction temperature and the reaction pressure are concerned.

In contrast to the reactions according to process varient (a) it is also possible to work in excess alcohol as the solvent if this alcohol is at the same time the reactant according to the formula (V). If the reactant of the formula (V) is a secondary amine, it is also possible to use a further equimolar amount of this amine, instead of an additional acid-neutralizing agent, to bind the hydrogen halide liberated in the reaction.

The following may be mentioned as new active compounds: thiocarbonic acid O-methyl S-4,5-dichloro-thiazolyl-(2) ester, thiocarbonic acid O-ethyl S-4,5-dichloro-thiazolyl-(2) ester, thiocarbonic acid O-propyl S-4,5-dichloro-thiazolyl-(2) ester, thiocarbonic acid O-isopropyl S-4,5-dichloro-thiazolyl-(2) ester, thiocarbonic acid O-butyl S-4,5-dichloro-thiazolyl-(2) ester, thiocarbonic acid O-isobutyl S-4,5-dichloro-thiazolyl-(2) ester, thiocarbonic acid O-sec.-butyl S-4,5-dichloro-thiazolyl-(2)ester, thiocarbonic acid O-tert.-butyl S-4,5-dichloro-thiazolyl-(2) ester, thiocarbonic acid O-pentyl S-4,5-dichloro-thiazolyl-(2) ester, thiocarbonic acid O-octyl S-4,5-dichloro-thiazolyl-(2)ester, thiocarbonic acid O-dodecyl S-4,5-dichloro-thiazolyl-(2) ester, thiocarbonic acid O-2-chloroethyl S-4,5-dichloro-thiazolyl-(2) ester, thiocarbonic acid O-2,2,2-trichloroethyl S-4,5-dichloro-thiazolyl-(2) ester, thiocarbonic acid O-1,2,2,2-tetrachloroethyl S-4,5-dichloro-thiazolyl-(2) ester, thiocarbonic acid O-1,3-dichloro-isopropyl S-4,5-dichloro-thiazolyl-(2) ester, thiocarbonic acid O-2,2,2-tribromoethyl S-4,5-dichloro-thiazolyl-(2) ester, thiocarbonic acid O-2,3-dibromo-propyl S-4,5-dichloro-thiazolyl-(2) ester, thiocarbonic acid O-2-methoxyethyl S-4,5-dichloro-thiazolyl-(2) ester, thiocarbonic acid O-2-isopropoxy-ethyl S-4,5-dichloro-thiazolyl-(2) ester, thiocarbonic acid O-2-phenoxy S-4,5-dichloro-thiazolyl (2) ester, thiocarbonic acid O-4-methoxy-butyl S-4,5-dichloro-thiazolyl-(2) ester, thiocarbonic acid O-2-methylmercaptoethyl S-4,5-dichloro-thiazolyl-(2) ester, thiocarbonic acid O-2-phenylmercapto-ethyl S-4,5-dichloro-thiazolyl-(2) ester, thiocarbonic acid O-4-chloro-phenylmercapto-ethyl S-4,5-dichloro-thiazolyl-(2) ester, thiocarbonic acid O-allyl S-4,5-dichloro-thiazolyl-(2) ester, thiocarbonic acid O-crotyl S-4,5-dichloro-thiazolyl-(2) ester, thiocarbonic acid O-2-methyl-buten-(3)-yl-(2) S-4,5-dichloro-thiazolyl-(2) ester, thiocarbonic acid O-propargyl S-4,5-dichloro-thiazolyl-(2) ester, thiocarbonic acid O-butyn-(1)-yl-(3) S-4,5-dichlorothiazolyl-(2) ester, thiocarbonic acid O-2-methyl-butyn-(3)-yl-(2) S-4,5-dichloro-thiazolyl-(2) ester, bis-thiocarbonic acid O,O-1,4-butylene ester S,S-bis-4,5-dichloro-thiazolyl ester, thiocarbonic acid O-benzyl S-4,5-dichloro-thiazolyl ester, thiocarbonic acid O-4-chloro-benzyl S-4,5-dichloro thiazolyl ester, thiocarbonic acid O-2,6-dichlorobenzyl S-4,5-dichloro-thiazolyl ester, thiocarbonic acid O-4-methylbenzyl S-4,5-dichloro-thiazolyl ester, thiocarbonic acid O-4-trifluoromethyl-benzyl S-4,5-dichloro-thiazolyl ester, thiocarbonic acid O-4-nitro-benzyl S-4,5-dichloro-thiazolyl ester, thiocarbonic acid O-4-methoxy-benzyl S-4,5-dichloro-thiazolyl ester, thiocarbonic acid O-4-methylmercapto benzyl S-4,5-dichloro-thiazolyl ester, thiocarbonic acid O-4-cyano-benzyl S-4,5-dichloro-thiazolyl ester, thiocarbonic acid O-2-phenylethyl S-4,5-dichloro-thiazolyl ester, thiocarbonic acid O-3-phenyl-propyl S-4,5-dichloro-thiazolyl ester, thiocarbonic acid O-diphenyl-methyl S-4,5-dichloro-thiazolyl ester, thiocarbonic acid O-1,2-diphenyl-ethyl S-4,5-dichloro-thiazolyl ester, thiocarbonic acid O-cyclobutyl S-4,5-dichloro-thiazolyl ester, thiocarbonic acid O-cyclopentyl S-4,5-dichloro-thiazolyl ester, thiocarbonic acid-O-cyclohexyl S-4,5-dichloro-thiazolyl ester, thiocarbonic acid O-cyclooctyl S-4,5-dichloro-thiazolyl ester, thiocarbonic acid O-cyclohexylmethyl S-4,5-dichloro-thiazolyl ester, thiocarbonic acid O-tetralyl-(1) S-4,5-dichloro-thiazolyl ester, thiocarbonic acid O-phenyl S-4,5-dichloro-thiazolyl ester, thiocarbonic acid O-2-chlorophenyl S-4,5-dichloro-thiazolyl ester, thiocarbonic acid O-4-chloro-phenyl S-4,5-dichloro-thiazolyl ester, thiocarbonic acid O-2,4-dichloro-phenyl S-4,5-dichloro-thiazolyl ester, thiocarbonic acid O-pentachlorophenyl S-4,5-dichloro-thiazolyl ester, thiocarbonic acid O-4-methyl-phenyl S-4,5-dichloro-thiazolyl ester, thiocarbonic acid O-2-methyl-4-chloro-phenyl S-4,5-dichloro-thiazolyl ester, thiocarbonic acid O-4-isopropyl-phenyl S-4,5-dichloro-thiazolyl ester, thiocarbonic acid O-2,6-di-tert.-butyl-4-methyl-phenyl S-4,5-dichloro-thiazolyl ester, thiocarbonic acid O-3-trifluoromethyl-phenyl S-4,5-dichloro-thiazolyl ester, thiocarbonic acid O-4-nitro-phenyl S-4,5-dichloro-thiazolyl ester, thiocarbonic acid O-4-methoxy-phenyl S-4,5-dichloro-thiazolyl ester, thiocarbonic acid O-3-methyl-4-methylmercapto-phenyl S-4,5-dichloro-thiazolyl ester, thiocarbonic acid O-4-dimethylamino-phenyl S-4,5-dichloro-thiazolyl ester, thiocarbonic acid O-4-carbethoxy-phenyl S-4,5-dichloro-thiazolyl ester, thiocarbonic acid O-4-N,N-dimethylcarbamoyl-phenyl S-4,5-dichloro-thiazolyl ester, thiocarbonic acid O-4-cyanophenyl S-4,5-dichloro-thiazolyl ester, thiocarbonic acid O-naphthyl-(1) S-4,5-dichloro-thiazolyl ester, thiocarbonic acid O-naphthyl-(2) S-4,5-dichloro-thiazolyl ester, dithiocarbonic acid S-methyl S-4,5-dichloro-thiazolyl ester, dithiocarbonic acid S-ethyl S-4,5-dichloro-thiazolyl ester, dithiocarbonic acid S-propyl S-4,5-dichloro-thiazolyl ester, dithiocarbonic acid S-isopropyl S-4,5-dichloro-thiazolyl ester, dithiocarbonic acid S-butyl S-4,5-dichloro-thiazolyl ester, dithiocarbonic acid S-dodecyl S-4,5-dichloro-thiazolyl ester, dithiocarbonic acid S-benzyl S-4,5-dichloro-thiazolyl ester, dithiocarbonic acid S-4-chloro-benzyl S-4,5-dichlorothiazolyl ester, dithiocarbonic acid S-3,4-dichloro-benzyl S-4,5-dichloro-thiazolyl ester, dithiocarbonic acid S-phenyl S-4,5-dichloro-thiazolyl ester dithiocarbonic acid S-4-chloro-phenyl S-4,5-dichloro-thiazolyl ester, dithiocarbonic acid S-4-methyl-phenyl S-4,5-dichloro-thiazolyl ester, dithiocarbonic acid O-ethyl S-4,5-dichloro-thiazolyl ester, dithiocarbonic acid O-butyl S-4,5-dichloro-thiazolyl ester, dithiocarbonic acid O-phenyl S-4,5-dichloro-thiazolyl ester, trithiocarbonic acid S-ethyl S-4,5-dichloro-thiazolyl ester, trithiocarbonic acid S-butyl S-4,5-dichloro-thiazolyl ester, trithiocarbonic acid S-benzyl S-4,5-dichloro-thiazolyl ester, trithiocarbonic acid S-phenyl S-4,5-dichloro-thiazolyl ester, N,N-dimethyl-thiocarbamic acid S-4,5-dichloro-thiazolyl ester, N,N-diethyl-thiocarbamic acid S-4,5-dichloro-thiazolyl ester, N,N-dipropyl-thiocarbamic acid S-4,5-dichloro-thiazolyl ester, N,N-diisopropyl-thiocarbamic acid S-4,5-dichloro-thiazolyl ester, N,N-dibutyl-thiocarbamic acid S-4,5-dichloro-thiazolyl ester, N-methyl-N-isopropyl-thiocarbamic acid S-4,5-dichloro-thiazolyl ester, N-methyl-N-dodecyl-thiocarbamic acid S-4,5-dichloro-thiazolyl ester, N-methyl-N-2-methoxyethyl-thiocarbamic acid S-4,5-dichloro-thiazolyl ester, N-methyl-N-2-methylmercapto-ethyl-thiocarbamic acid S-4,5-dichloro-thiazolyl ester, N-methyl-N-2-phenoxy-ethyl-thiocarbamic acid S-4,5-dichloro-thiazolyl ester, N,N-bis-2-cyanoethyl-thiocarbamic acid S-4,5-dichloro-thiazolyl ester, N,N-diallyl-thiocarbamic acid S-4,5-dichloro-thiazolyl ester, N,N-dicyclohexyl-thiocarbamic acid S-4,5-dichloro-thiazolyl ester, N-methyl-N-cyclohexyl-thiocarbamic acid S-4,5-dichloro-thiazolyl ester, N-methyl-N-phenyl-thiocarbamic acid S-4,5-dichloro-thiazolyl ester, N-methyl-N-4-chloro-phenyl-thiocarbamic acid S-4,5-dichloro-thiazolyl ester, N-methyl-N-4-methyl-phenyl-thiocarbamic acid S-4,5-dichloro-thiazolyl ester, N-methyl-N-4-methoxy-phenyl-thiocarbamic acid S-4,5-dichloro-thiazolyl ester, N-methyl-N-4-methylmercapto-phenyl-thiocarbamic acid S-4,5-dichloro-thiazolyl ester, N-methyl-N-4-nitro-phenyl-thiocarbamic acid S-4,5-dichloro-thiazolyl ester, pyrrolidine-1-thiocarboxylic acid S-4,5-dichloro-thiazolyl ester, piperidine-1-thiocarboxylic acid S-4,5-dichloro-thiazolyl ester, hexamethyleneimine-1-thiocarboxylic acid S-4,5-dichloro-thiazolyl ester, tetrahydroquinoline-1-thiocarboxylic acid S-4-5-dichloro-thiazolyl ester, imidazole-1-thiocarboxylic acid S-4,5-dichloro-thiazolyl ester, 1,2,4-triazole-1-thiocarboxylic acid S-4,5-dichloro-thiazolyl ester, morpholine-4-thiocarboxylic acid S-4,5-dichloro-thiazolyl ester, thiamorpholine-4-thiocarboxylic acid S-4,5-dichloro-thiazolyl ester, N,N-dimethyldithiocarbamic acid 4,5-dichloro-thiazolyl ester, N,N-diethyldithiocarbamic acid 4,5-dichloro-thiazolyl ester, N,N-dipropyl-dithiocarbamic acid 4,5-dichloro-thiazolyl ester, piperidine-1-dithiocarboxylic acid 4,5-dichloro-thiazolyl ester, morpholine-4-dithiocarboxylic acid 4,5-dichloro-thiazolyl ester and 2-thiocyanato-4,5-dichloro-thiazole.

The preparation of the compounds of this invention is illustrated in the following preparative Examples

EXAMPLE 1

O-methyl 4,5-dichloro-thiazolyl-(2) ester

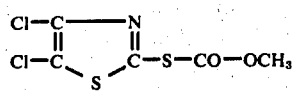 (1)

9.5 g (0.1 mole) of chloroformic acid methyl ester were added dropwise to a mixture of 18.6 g (0.1 mole) of 2-mercapto-4,5-dichloro-thiazole in 200 ml of acetone and 4 g (0.1 mole) of sodium hydroxide in 10 ml of water at 10°–15° C, whilst cooling. The mixture was stirred further for 2 hours at room temperature and was then diluted with 500 ml of water. The oil which separated out was taken up in chloroform and the chloroform solution was dried and distilled. Boiling point: 115°–121° C/0.1 mm Hg. Yield: 13 g (53% of theory) of thiocarbonic acid O-methyl 4,5-dichloro-thiazolyl-(2) ester. The following compounds could be prepared analogously:

EXAMPLE 2

Thiocarbonic acid O-ethyl S-4,5-dichloro-thiazolyl-(2) ester, boiling point: 88°–92° C/0.06 mm Hg.

EXAMPLE 3

Thiocarbonic acid O-isopropyl S-4,5-dichloro-thiazolyl-(2) ester, boiling point: 112°–116° C/0.1 mm Hg.

EXAMPLE 4

Thiocarbonic acid O-n-butyl S-4,5-dichloro-thiazolyl-(2) ester, boiling point: 123°–125° C/0.1 mm Hg; melting point: 27°–28° C.

EXAMPLE 5

Thiocarbonic acid O-phenyl S-4,5-dichloro-thiazolyl-(2) ester, melting point: 60°–62° C.

EXAMPLE 6

Thiocarbonic acid-O-isobutyl S-1,5-dichloro-thiazolyl-(2) ester, boiling point: 124°–126° C/0.07 mm Hg melting point: 31°–32° C.

EXAMPLE 7

Thiocarbonic acid-O-pentyl S-4,5-dichloro-thiazolyl-(2) ester, boiling point: 136° C/0.09 mm Hg.

EXAMPLE 8

Thiocarbonic acid O-dodecyl S-4,5-dichloro-thiazolyl-(2) ester, melting point: 28°–30° C (propanol).

EXAMPLE 9

Thiocarbobic acid O-2-chloro-ethyl S-4,5-dichloro-thiazolyl-(2) ester; boiling point: 165°–167° C/0.1 mm Hg.

EXAMPLE 10

Thiocarbonic acid O-1,3-dichlorl-isopropyl S-4,5-dichloro-thiazolyl-(2) ester; boiling point: 142°–143° C/0.1 mm Hg; melting point 102°–105° C.

EXAMPLE 11

Bis-thiocarbonic acid O,O-1,4-butylene ester S,S-bis-4,5-dichloro-thiazolyl-(2) ester; melting point 120°–123° C (petroleum ether).

EXAMPLE 12

Thiocarbonic acid O-benzyl S-4,5-dichloro-thiazolyl-(2) ester; boiling point: 158°–162° C/0.065 mm Hg.

EXAMPLE 13

Thiocarbonic acid O-cyclohexylmethyl S-4,5-dichlorothiazolyl-(2) ester; boiling point: 175°–177° C/0.085 mm Hg.

EXAMPLE 14

Thiocarbonic acid O-4-chloro-phenyl S-4,5-dichloro-thiazolyl-(2) ester; melting point: 122°–125° C (butanol).

EXAMPLE 15

Thiocarbonic acid O-2-methyl-4-chloro-phenyl S-4,5-dichloro-thiazolyl-(2) ester; melting point: 86°–89° C (butanol).

EXAMPLE 16

Dithiocarbonic acid S-butyl S-4,5-dichloro-thiazolyl-(2) ester; boiling point: 148° C/0.08 mm Hg.

EXAMPLE 17

Dithiocarbonic acid S-4-chloro-phenyl S-4,5-dichloro-thiazolyl-(2) ester; melting point: 86°–88° C (petroleum ether).

EXAMPLE 18

N,N-dimethyl-thiocarbamic acid S-4,5-dichloro thiazolyl ester

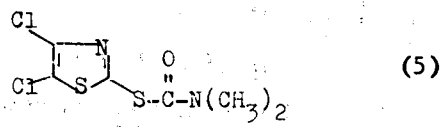 (5)

10.75 g (0.1 mole) of dimethylcarbamic acid chloride were added to a suspension of 20.8 g (0.1 mole) of the sodium salt of 2-mercapto-4,5-dichloro-thiazole in 100 ml of dioxane and the mixture was stirred for 5 hours at 70° C. After cooling, 500 ml of water were added. The crystals which had separated out were filtered off and recrystallized from butanol. Yield: 22 g (85% of theory) (N,N-dimethyl-thiocarbamic acid S-4,5-dichloro-thiazolyl ester) of melting point: 151°–153° C.

EXAMPLE 19

Analogously, dimethylthiocarbamic acid chloride gave dimethyl-dithiocarbamic acid S-4,5-dichloro-thiazolyl-(2) ester, melting point: 130°–131° C (from petroleum ether).

EXAMPLE 20

N,N-diethyl-thiocarbamic acid S-4,5-dichlorothiazolyl ester

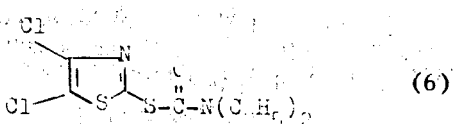 (6)

14.6 g (0.2 mole) of diethylamine were added dropwise to a solution of 24.8 g (0.1 mole) of thiocarbonic acid S-4,5-dichloro-thiazolyl ester chloride in 100 ml of dioxane at 10°–15° C, whilst cooling with ice. After the exothermic reaction had subsided, the mixture was stirred further for 1 hour at room temperature and was then evaporated in vacuo. The residue treated with water was recrystallized from petroleum ether. Yield: 12 g (42% of theory) of melting point: 101°–103° C.

EXAMPLE 21

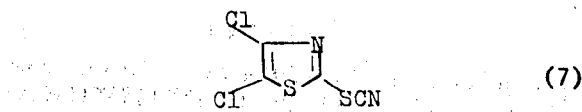 (7)

7 g (0.114 mole) of cyanogen chloride were added dropwise to a mixture of 18.6 g (0.1 mole) of 2-mercapto-4,5-dichloro-thiazole in 100 ml of dioxane and 4 g of NaOH in 10 ml of water at 10°–15° C, whilst cooling. The mixture was stirred further for 3 hours at room temperature and poured onto ice water, and the product was filtered off. Yield: 16 g (76% of theory of 2-thiocyanato-4,5-dichloro-thiazole of melting point: 86°–88° C (from petroleum ether).

PREPARATION OF THE STARTING MATERIALS a. 2-Mercapto-4,5-dichloro thiazole

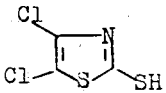

A solution of 94g (0.5 mole) of trichloro-thiazole in 250 ml of dioxane was added dropwise to a solution of 56 g (1 mole) of sodium hydrogen sulphide in 450 ml of water at room temperature, whilst stirring. In the course thereof, the temperature rose to about 35° C. The mixture was stirred for a further 2 hours at 50°–60° C and was then poured into 2 liters of ice water. The completely clear solution was acidified with dilute hydrochloric acid and the solid product which had precipitated was filtered off and dried. Yield: practically quantitative. Melting point: 132°–133° C (petroleum ether). b. Thiocarbonic acid S-4,5-dichloro-thiazolyl ester chloride

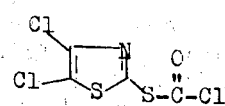

20.8 g (0.1 mole) of the sodium salt of 2-mercapto-4,5-dichloro-thiazole, obtained from 2-mercapto-4,5-dichloro-thiazole in methanol with a stoichiometric amount of sodium methylate, were introduced at room temperature in 150 ml of toluene which had been saturated with phosgene at room temperature. In the course of the introduction, the temperature rose to 35°–40° C. The mixture was additionally stirred further for 1 hour at 40° C in a stream of phosgene, the sodium chloride which had separated out was filtered off and the filtrate was evaporated in vacuo. Yield: 24 g (71.5% of theory); melting point: 66°–68° C (petroleum ether).

As stated above, the active compounds according to the invention exhibit strong herbicidal properties. They can be used for destroying weeds.

Weeds in the broadest sense are plants which grow in crops or other locations where they are not desired. Whether the active compounds according to the invention act as total herbicides or as selective herbicides depends essentially on the amount used.

The compounds according to the invention can be used, for example, with the following plants: dicotyledons such as mustard (Sinapis), cress (Lepidium), cleavers (Galium), chickweed (Stellaria), camomile (Matricaria), gallant soldier (Galinsoga), goosefoot (Chenopodium), annual nettle (Urtica), groundsel (Senecio), cotton (Gossypium), beets (Beta), carrots (Daucus), beans (Phaseolus), potatoes (Solanum) and coffee (Coffea); monocotyledons such as timothy (Phleum), bluegrass (Poa), fescue (Festuca), goosegrass (Eleusine), foxtail (Setaria), ryegrass (Lolium), cheat (Bromus), barnyard grass (Echinochloa), corn (Zea), rice (Oryza), oats (Avena), barley (Hordium), wheat (Triticum), millet (Panicum) and sugar cane (Saccharum).

The active compounds according to the invention are particularly suitable for the selective combating of weeds in carrots, cereals and beans.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulphoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulphonates, alkyl sulphates and aryl sulphonates as well as albumin hydrolyzation products; and preferred examples of dispersing agents include lignin sulphite waste liquors and methyl cellulose.

The active compounds according to the invention can be present in the formulations as a mixture with other active compounds.

The formulations in general contain from 0.1 to 95 per cent by weight of active compound, preferably from 0.5 to 90 percent by weight.

The active compounds can be used as such, in the form of their formulations or as the use forms prepared therefrom, such as ready-to-use solutions, emulsions, suspensions, powders, pastes and granules. They may be used in the customary manner, for example by watering, spraying, atomizing, scattering or dusting. They are preferably used after the emergence of the plants.

The amount of active compound employed can vary within fairly wide ranges; it depends essentially on the nature of the desired effect. In general, the amounts used are between 0.1 and 15 kg/ha, preferably between 0.2 and 8 kg/ha.

Some of the active compounds according to the invention also display a fungicidal activity.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier. It will be seen that the usual methods of providing a harvested crop may be improved by the present invention.

The herbicidal activity of the present compounds is illustrated in the following biotest Example, in which the active compounds are identified by a number which is co-related with the appropriate formula in a subsequent table.

EXAMPLE A Post-emergence test Solvent: 5 parts by weight of acetone Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants, which had a height of 5–15 cm, were sprayed with the preparation of the active compound in such a way as to apply the amounts of active compound per unit area which are indicated in the table. Depending on the concentration of the spray liquor, the amount of water used was between 1,000 and 2,000 l/ha. After three weeks, the degree of damage to the plants was determined and characterized by the values 0–5, which have the following meaning:

0 no effect
1 a few slightly burnt spots
2 marked damage to leaves
3 some leaves and parts of stalks partially dead
4 plant partially destroyed
5 plant completely dead.

The active compounds, the amounts used and the results can be seen from Table A which follows:

Table A

Post-emergence test

| Active compound | Amount of active compound used, kg/ha | Echinochloa | Chenopodium | Sinapis | Galinsoga | Stellaria | Urtica | Carrots | Cotton | Wheat | Beans |
|---|---|---|---|---|---|---|---|---|---|---|---|
| (1) | 2 | 5 | 4–5 | 5 | 5 | 5 | 5 | 3 | 4–5 | 1–2 | 3 |
|  | 1 | 5 | 4 | 5 | 2 | 4 | 3 | 3 | 4–5 | 0 | 2 |
| (2) | 2 | 4–5 | 5 | 5 | 5 | 4–5 | 5 | 2 | 3 | 3 | 1 |
|  | 1 | 3 | 4–5 | 5 | 5 | 4 | 5 | 2 | 3 | 2 | 0 |

Table A-continued

Post-emergence test

| Active compound | Amount of active compound used, kg/ha | Echino-chloa | Cheno-podium | Sina-pis | Galin-soga | Stella-ria | Urtica | Carrots | Cotton | Wheat | Beans |
|---|---|---|---|---|---|---|---|---|---|---|---|
| (3) | 2 | 4–5 | 4–5 | 5 | 5 | 4–5 | 5 | 0 | 4–5 | 3 | 3 |
|  | 1 | 4 | 4–5 | 5 | 5 | 3 | 5 | 0 | 3 | 2 | 2 |
| (4) | 2 | 4–5 | 5 | 5 | 5 | 5 | 5 | 2 | 5 | 2 | 2 |
|  | 1 | 4 | 4–5 | 5 | 5 | 5 | 5 | 2 | 4 | 0 | 2 |

Table of active compounds (1) Cl—C=N, Cl—C(S)—C—S—CO—OCH₃

(2) Cl—C=N, Cl—C(S)—C—S—CO—OC₂H₅

(3) Cl—C=N, Cl—C(S)—C—S—CO—O—CH(CH₃)₂

(4) Cl—C=N, Cl—C(S)—C—S—CO—OC₄H₉-n

It will be understood that the specification and examples are illustrative but not limitative of the present invention and that other embodiments within the spirit and scope of the invention will suggest themselves to those skilled in the art.

What is claimed is:

1. 2-Mercapto-4,5-dichloro-thiazole compound of the formula

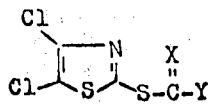

(I)

in which

X is oxygen or sulfur

Y is a radical -OR, -SR or

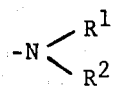

R is alkyl of from 1 to 12 carbon atoms optionally substituted by one or more substituents selected from chlorine, bromine, lower alkoxy, phenoxy, lower alkylmercapto and phenylmercapto; or R is alkenyl of from 2 to 6 carbon atoms or alkynyl of from 3 to 6 carbon atoms; or R is aralkyl of from 1 or 2 phenyl radicals on the alkyl moiety and 1 to 4 carbon atoms in the alkyl moiety, the phenyl moiety optionally substituted by one or more substituents selected from chlorine, methyl, trifluoromethyl, nitro, methoxy, methylmercapto and cyano; or R is cycloalkyl of from 4 to 7 carbon atoms wherein the ring may be substituted by methyl or a fused benzene ring; or R is aryl of up to 10 carbon atoms optionally substituted by one or more radicals selected from chlorine, lower alkyl, trifluoromethyl, nitro, methoxy, methylmercapto, dimethylamino, carbethoxy, N,N-dimethyl-carbamoyl and cyano; and $R^1$ and $R^2$ are alkyl of from 1 to 12 carbon atoms, optionally substituted by a substituent selected from methoxy, methylmercapto, phenoxy and cyano; alkyl, cyclohexyl, or phenyl, the phenyl ring being optionally substituted by a substituent selected from chlorine, methyl, methoxy methylmercapto and nitro; or $R^1$ and $R^2$ together with the adjoining nitrogen represent a member selected from the group consisting of pyrrolidin-1-yl, piperidin-1-yl, hexamethylenimin-1-yl, tetrahydroquinolin-1-yl, imidazol-1-yl, 1,2,4-triazol-1-yl, morpholin-4-yl and thiamorpholin-4-yl; and X and Y together represent a triply bonded nitrogen atom.

2. 2-Mercapto-4,5-dichloro-thiazole compound as claimed in claim 1 wherein X is oxygen.

3. 2-Mercapto-4,5-dichloro-thiazole compound as claimed in claim 1 wherein X is sulfur.

4. 2-Mercapto-4,5-dichloro-thiazole compound as claimed in claim 1 wherein Y is the -OR radical.

5. 2-Mercapto-4,5-dichloro-thiazole compound as claimed in claim 1 wherein Y is the -SR radical.

6. 2-Mercapto-4,5-dichloro-thiazole compound as claimed in claim 1 wherein Y is

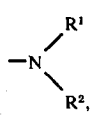

7. 2-Mercapto-4,5-dichloro-thiazole compound as claimed in claim 1 wherein X and Y taken together represent a triply bonded nitrogen atom.

8. 2-Mercapto-4,5-dichloro-thiazole compound as claimed in claim 1 designated thiocarbonic acid O-methyl 4,5-dichlorothiazolyl(2) ester.

9. 2-Mercapto-4,5-dichloro-thiazole compound as claimed in claim 1 designated thiocarbonic acid O-ethyl S-4,5-dichloro-thiazolyl-(2) ester.

10. 2-Mercapto-4,5-dichloro-thiazole compound as claimed in claim 1 designated thiocarbonic acid O-isopropyl S-4,5-dichloro-thiazolyl-(2) ester.

11. 2-Mercapto-4,5-dichloro-thiazole compound as claimed in claim 1 designated thiocarbonic acid O-n-butyl S-4,5-dichloro-thiazolyl-(2) ester.

12. 2-Mercapto-4,5-dichloro-thiazole compound as claimed in claim 1 designated thiocarbonic acid O-2-chloroethyl S-4,5-dichloro-thiazolyl-(2) ester.

13. 2-Mercapto-4,5-dichloro-thiazole compound as claimed in claim 1 designated dithiocarbonic acid S-butyl S-4,5-dichloro-thiazolyl-(2) ester.

14. 2-Mercapto-4,5-dichloro-thiazole compound as claimed in claim 1 designated N,N-dimethyl-thiocarbamic acid S-4,5-dichloro-thiazolyl ester.

15. 2-Mercapto-4,5-dichloro-thiazole compound as claimed in claim 1 designated dimethyl-dithiocarbamic acid S-4,5-dichloro-thiazolyl-(2) ester.

16. 2-Mercapto-4,5-dichloro-thiazole compound as claimed in claim 1 wherein
X is oxygen or sulfur,
X is a radical -OR, -SR or

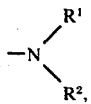

wherein
R is alkyl or chloroalkyl of from 1 to 12 carbon atoms; or
R is benzyl, cyclohexyl, or methylbenzyl or methylcyclohexyl; or
R is phenyl, chlorophenyl, or methylphenyl; and
$R^1$ and $R^2$ are alkyl of from 1 to 12 carbon atoms; and
X and Y together represent a triply bonded nitrogen atom.

17. Bis-thiocarbonic acid 0,0-1,4-butylene ester S,S-bis-4,5-dichloro-thiazolyl-(2) ester of the formula

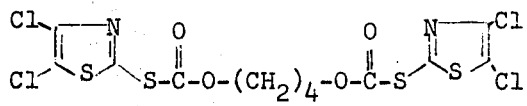

* * * * *